(12) United States Patent
Schubert et al.

(10) Patent No.: US 6,584,174 B2
(45) Date of Patent: Jun. 24, 2003

(54) REGISTERING IMAGE INFORMATION

(75) Inventors: Mario Schubert, Landsham/Pliening (DE); Falko Seifferth, Zorneding (DE); Stefan Vilsmeier, Kufstein (AT); Mario Zeiss, Poing (DE)

(73) Assignee: BrainLAB AG, Kirchheim/Heimstetten (DE)

( * ) Notice: Subject to any disclaimer, the term of this patent is extended or adjusted under 35 U.S.C. 154(b) by 0 days.

(21) Appl. No.: 10/002,956

(22) Filed: Nov. 1, 2001

(65) Prior Publication Data

US 2002/0176541 A1 Nov. 28, 2002

(30) Foreign Application Priority Data

May 22, 2001 (EP) .............................................. 01111988

(51) Int. Cl.$^7$ ................................ A61B 6/00; H05G 1/28
(52) U.S. Cl. ............................ 378/165; 378/8; 378/20; 378/205; 378/207; 382/131; 382/291; 382/294
(58) Field of Search ................................. 378/8, 20, 42, 378/162, 165, 166, 205, 206, 207; 382/131, 291, 294

(56) References Cited

U.S. PATENT DOCUMENTS

| | | | | |
|---|---|---|---|---|
| 5,369,678 A | * | 11/1994 | Chiu et al. ............... | 378/62 |
| 5,446,548 A | | 8/1995 | Gerig et al. ............... | 356/375 |
| 5,730,129 A | * | 3/1998 | Darrow et al. ............ | 600/407 |
| 5,799,055 A | | 8/1998 | Peshkin et al. ............ | 378/42 |
| 6,092,928 A | * | 7/2000 | Mattson et al. ........... | 378/205 |
| 6,120,180 A | * | 9/2000 | Graumann ................ | 378/206 |
| 6,139,183 A | * | 10/2000 | Graumann ................ | 378/206 |
| 6,206,566 B1 | * | 3/2001 | Schuetz ..................... | 378/205 |
| 6,213,638 B1 | * | 4/2001 | Rattner ..................... | 378/198 |
| 6,442,230 B1 | * | 8/2002 | Wilting et al. ............. | 378/20 |

FOREIGN PATENT DOCUMENTS

| | | |
|---|---|---|
| DE | 199 17 867 A | 11/2000 |
| WO | 00/56215 | 9/2000 |

* cited by examiner

Primary Examiner—Drew A. Dunn
Assistant Examiner—Allen C. Ho
(74) Attorney, Agent, or Firm—Renner, Otto, Boisselle & Sklar, LLP

(57) ABSTRACT

The invention relates to a method for registering image information by means of a medical navigation system, wherein:

current image information, in particular a current x-ray image of a patient to be registered using the navigation system, is produced;

the position of the image information detection device, in particular of the x-ray device, is established by means of the navigation system;

the current image information, in particular the current x-ray image, is compared with the aid of a computer with other image information (for example, a previously taken x-ray image);

in the event of a difference between the image content of the current and previous image, the new relative position of the image information detection device or x-ray device respectively and of the patient is detected and stored; and the current image information produced or current x-ray image produced, respectively, is registered in the navigation system, based on the information on the new relative position.

The invention further relates to: a program which, when run on a computer or loaded in a computer, causes the computer to carry out the method; a computer program storage medium comprising such a program; and an x-ray image registering means.

15 Claims, 1 Drawing Sheet

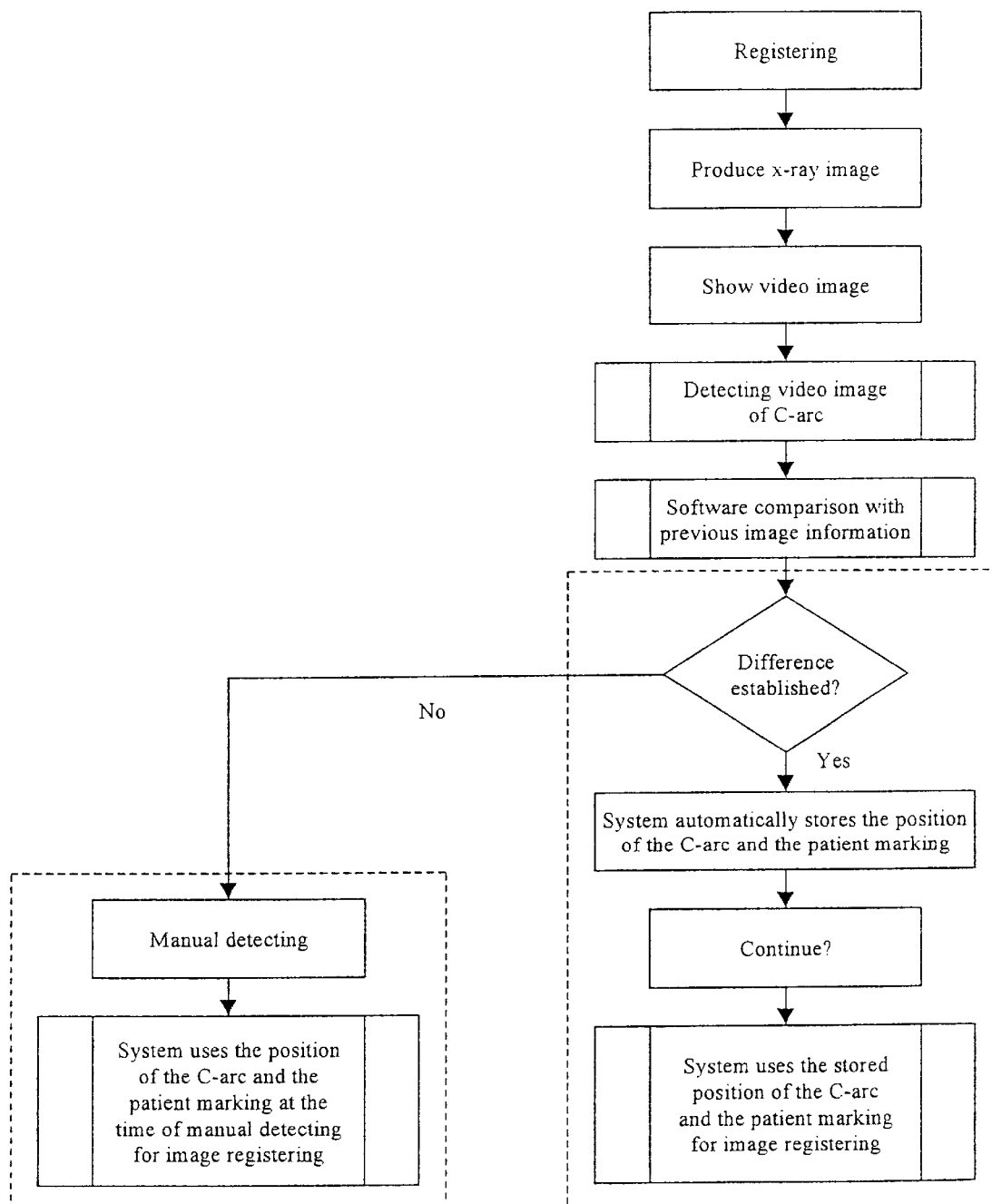

REGISTERING IMAGE INFORMATION

FIELD OF THE INVENTION

The present invention relates to registering image information. In particular, the invention relates to a method for registering and/or re-registering an x-ray image by means of: a medical navigation system; a program which, when run on a computer or loaded in a computer, causes the computer to carry out the method; a computer program storage medium comprising such a program; and an x-ray image registering means.

BACKGROUND OF THE INVENTION

During medical treatments in which the position of the patient or of parts of the patient's body are tracked by means of a navigation system, i.e. are determined, and in particular in which instruments are also tracked using the navigation system, it is necessary to register the patient at the exact time of image acquisition, for instance recording an x-ray image, since the patient cannot always be prevented from moving, or being moved, or specific areas of the patient prevented from moving (for example, through breathing). Registration is achieved, for example, by producing a current x-ray image of the patient, which is then in turn registered in the navigation system with the aid of arrangements of markings. Using the x-ray image and its registered position, current information is then available on the current positioning of the patient, and the patient can be navigated and treated using said current data.

In connection with the above measures, it is very important to know what point in time an x-ray image was produced at, in order to register the current state. In a known system, the so-called FluoroNav system of the firm Sofamor Danek, a special x-ray sensitive sensor is used to automatically register the position of the x-ray device, a C-arc apparatus and the arrangement of patient markers, when an x-ray image is produced using the C-arc. Because of the need to provide a sensor and the corresponding signal transfer alone, this method is costly, expensive and susceptible to error.

Another method currently used is based on manual input, i.e. the navigation and/or computer system is told by the "push of a button" that an x-ray image has been produced and this x-ray image needs to be registered. Upon this input, the C-arc and the patient are registered, i.e. their relative position is determined, by the navigation system, for example via camera images, by means of arrangements of markers arranged on the C-arc and on the patient.

This method disadvantageously leads to a time delay between producing the (new) x-ray image with the C-arc and actually registering it through the navigation system. Since it is possible for the patient to move during this period of time, or for his marker means to be shifted by the process of breathing alone, the intermediate image detection by the cameras around the time elapsed during manual registering can lead to inaccuracy in re-registering, which would then also make navigation inaccurate.

With respect to the technical background of the invention, the U.S. Pat. Nos. 5,799,055; 3,577,160; 5,784,431; 5,967,982; 5,772,594 may be cited, which deal with registering x-ray images in the context of surgical navigation methods, as well as U.S. Pat. No. 6,118,845 which describes a system and method for reducing and eliminating image interference while calibrating x-ray image forming devices.

SUMMARY OF THE INVENTION

It is the object of the present invention to develop the registering of image information, in particular of an x-ray images in the above context, in such a way as to overcome the disadvantages mentioned. Preferably, registering should be technically cost-effective, and in particular registering with high precision should be made possible.

This object is solved in accordance with the invention by a method for registering image information, in particular an x-ray image, by means of a medical navigation system, wherein:

current image information, in particular a current x-ray image, of a patient to be registered using the navigation system is produced;

the position of the image information detection device, in particular of the x-ray device, is established by means of the navigation system;

the current image information, in particular the current x-ray image, is compared with the aid of a computer with other image information (for example, a previously taken x-ray image);

in the event of a difference between the image content of the current and previous image, the new relative position of the image information detection device or x-ray device respectively is detected and stored; and the current image information produced or current x-ray image produced respectively is registered in the navigation system, based on the information on the new relative position.

Where embodiments of the invention are described in the following using terms such as "x-ray image" and "x-ray device", these terms are only to be understood as examples of suitable image information and detection devices, for example CT, MR, ultrasound, SPECT, PET.

Thus, in the method in accordance with the invention, the system recognises with the aid of a computer whether a change in the patient's position has taken place in a new x-ray image. The criterion for comparison here is the difference in image content between the current and previous image information, and it is particularly advantageous that re-registering only has to be carried out when a difference in image content is actually present. In this way, a much more meaningful deciding criterion is chosen, than for example if re-registering is performed by means of a sensor every time an x-ray is produced. Moreover, the system can quickly establish whether a difference in image content is present, such that the time gap mentioned previously, i.e. the time that elapses between producing the image and registering by manual input, can be eliminated, and registering therefore made very accurate. A first or initial registering can of course also take place. A difference in image information is also present then, since no previous image is available.

The invention also offers the possibility of registering accurately without expensive technical costs (sensor and signal transfer).

In a preferred embodiment of the method in accordance with the invention, the navigation system registers and re-registers the patient and/or the x-ray device by detecting markings arranged on the patient or the x-ray device respectively, in particular arrangements of reflection markers, with the aid of cameras.

Preferably, registering in the navigation system takes place purely on the software side and, as already mentioned above, comparison of the image contents and registering take place automatically and without prompting by the operator.

The invention further relates to a program which, when run on a computer or loaded in a computer, causes the computer to carry out the method as described above. The invention further relates to a computer program storage medium, such as for example a CD, a DVD or a diskette, comprising a corresponding program.

In accordance with a further aspect of the invention, the invention relates to an x-ray image registering means comprising a medical navigation system, an x-ray device with which a current x-ray image is produced of a patient to be registered using the navigation system, the navigation system including a means by which the position of the x-ray device is established, characterised by an image comparing means with which the current x-ray image is compared with the aid of computers with previously recorded image information, as well as by a detecting and storing means with which, in the event of a difference between the image content of the current and previous image information, the new relative position of the x-ray device and the patient is detected and stored, wherein, the current x-ray image produced can be registered in the navigation system, based on the information on the new relative position.

It is also perfectly conceivable within the context of the invention to use an image from an ultrasound device instead of an x-ray image, and to register this/these image/s accordingly. Other transillumination or image forming methods may also be used.

DESCRIPTION OF THE FIGURE

In the sole FIGURE of the appended drawing, there is provided a flowchart depicting a sequence of steps in accordance with an embodiment of the invention.

DETAILED DESCRIPTION OF THE INVENTION

The invention will now be explained in more detail by way of a sequence of the method shown as an example, wherein reference is made to the flow chart enclosed.

The layout is as follows:

A patient, on whom an arrangement of markings is arranged in the vicinity of the area to be treated, is lying on a patient bed and is to be treated, wherein the treatment is assisted by a navigation system which detects and tracks the position of the patient with the aid of the aforementioned arrangement of markers, also the position of instruments for treatment and treatment devices respectively and in particular the position of a C-arc x-ray device, again via arrangements of markers fixed to said instruments and devices.

Registering is then firstly carried out, i.e. the position of the patient is detected relative to the x-ray image. The position of the patient and of the C-arc x-ray device is continuously detected. An x-ray image is then made, and the overall layout is shown in a video image. A video unit assigned to the navigation system serves this purpose, and obtains additional positional information. The video image with the C-arc x-ray device is likewise detected by the navigation system, and this information is used to calculate the position of the x-ray image in 3-D space and to enable navigation including the x-ray image information.

If all the above information is then available, it may be necessary to carry out registering once or even a number of times during treatment, for example in order to compensate for patient movement. To this end, a new x-ray image is produced, and at this point intercedes. If it exhibits a sufficient image quality, the x-ray image is compared with the previously available image information by means of image processing carried out on the computer of the navigation system (software-comparison). If this establishes a difference in image content, the system automatically stores the position of the C-arc and the patient, which is known to the navigation system at any point in time by detecting the arranged markings. The treatment can then be continued, the system using the new stored position of the C-arc and patient for x-ray image registering.

If no difference in image content is established in the deciding step described above, registering can also be performed manually according to the previous method. For image registering, the system uses the position of the C-arc and patient existing at that point in time.

Thus, the system has stored the position of the C-arc and patient, and will calculate a highly accurate position in 3-D space for the x-ray image, even when the patient or C-arc has been moved, this in turn allowing highly accurate navigation.

What is claimed is:

1. A method for registering and/or re-registering image information by means of a medical navigation system, wherein:

current image information of a patient to be registered using the navigation system is produced using an image information detection device;

the position of the image information detection device is established by means of the navigation system;

the current image information is compared with the aid of a computer with previously acquired image information;

in the event of a difference between the image content of the current and previously acquired image information, a new relative position of the image information detection device and the patient is detected and stored; and the current image information produced is registered in the navigation system, based on the information on the new relative position.

2. The method as set forth in claim 1, wehrein the position of the image information detection device and patient is continuously stored in the course of acquiring current image information of the patient, when a difference in the image content is established, while this does not occur when such a difference is not established, work (registering) then continuing using the previously acquired image information.

3. The method as set forth in claim 1, wherein the navigation system registers and re-registers the patient by detecting markings arranged on the patient or the image inforamtion detection device with the aid of cameras.

4. The method as set forth in claim 1, wherein registering in the navigation system takes place purely on the software side.

5. The method as set forth in claim 1, wherein comparison of the image contents and registering take place automatically and without prompting by the operator.

6. A program which, when run on a computer or loaded in a computer, causes the computer to carry out the method in accordance with claim 1.

7. A computer program storage medium comprising the program as set forth in claim 6.

8. An x-ray image registering means comprising a medical navigation system, an x-ray device with which a current x-ray image is produced of a patient to be registered using the navigation system, the navigation system including a means by which the position of the x-ray device is established, characterised by an image comparing means with which the current x-ray image is compared with the aid of computers with previous image information, as well as by a detecting and storing means with which, in the event of a difference between the image content of the current and previous image information, the new relative position of the x-ray device and the patient is detected and stored, whereby the current x-ray image produced can be highly accurately re-registered in the navigation system, based on the information on the new relative position.

9. The method as set forth in claim 1, wherein the image information detection device is an x-ray device.

10. The method as set forth in claim 9, wherein the x-ray device is a C-arc x-ray device.

11. A method for registering image information by means of a medical navigation system, comprising the steps of:

using an image information detection device to acquire current image information of a patient;

comparing the current image information with previously acquired image information of the patient to determine if a difference exists between the compared image information; and in the event of a difference between the image content of the current and previously acquired image information, registering the current image information of the patient in the navigation system based on current positions of the image information detection device and the patient as determined by the navigation system.

12. The method as set forth in claim 11, wherein the image information detection device is an x-ray device.

13. The method as set forth in claim 12, wherein the x-ray device is a C-arc x-ray device.

14. A program which, when run on a computer, causes the computer to carry out the method in accordance with claim 11.

15. A computer program storage medium comprising the program as set forth in claim 14.

* * * * *